(12) United States Patent
Ivanov

(10) Patent No.: US 8,088,055 B2
(45) Date of Patent: Jan. 3, 2012

(54) PLAN-BASED MEDICAL IMAGE REGISTRATION FOR RADIOTHERAPY

(75) Inventor: Yuri Ivanov, Arlington, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 46 days.

(21) Appl. No.: 12/785,626

(22) Filed: May 24, 2010

(65) Prior Publication Data

US 2011/0284771 A1  Nov. 24, 2011

(51) Int. Cl.
*A61N 5/00* (2006.01)
(52) U.S. Cl. .......................................................... 600/1
(58) Field of Classification Search ............... 600/1–8, 600/407, 425, 427; 250/491.1; 378/20, 68, 378/177–180, 195, 205–206
See application file for complete search history.

(56) References Cited

U.S. PATENT DOCUMENTS

| | | | | |
|---|---|---|---|---|
| 7,199,382 B2 * | 4/2007 | Rigney et al. | | 250/492.1 |
| 7,207,715 B2 * | 4/2007 | Yue | | 378/205 |
| 7,860,550 B2 * | 12/2010 | Saracen et al. | | 600/410 |
| 7,934,869 B2 * | 5/2011 | Ivanov et al. | | 378/205 |

* cited by examiner

*Primary Examiner* — John Lacyk
(74) *Attorney, Agent, or Firm* — Dirk Brinkman; Gene Vinokur

(57) ABSTRACT

A method determines an error in aligning a patient with a radiation beam. A planning volume V is acquired during treatment planning, and a treatment volume I is acquired during treatment. For each point r in the planning volume and treatment volume to be aligned by a coordinate transformation T, a weighted error DWE is minimized using an objective function F(r, T) applied to the planning volume and the treatment volume weighted by a weighting function W(r) as $$WE(T) = \sum_r W(r) F(r, T),$$

where W(r) is a function of a target weight $W_T$, a tissue at risk weight $W_R$, and a delivered dose weight $W_D$.

4 Claims, 2 Drawing Sheets

PLAN-BASED MEDICAL IMAGE REGISTRATION FOR RADIOTHERAPY

FIELD OF THE INVENTION

This invention relates generally to radiation treatment planning, and more particularly to plan-based medical image registration.

BACKGROUND OF THE INVENTION

When a patient is to receive radiation treatment, the patient needs to be carefully aligned with the iso-center of the radiation beam. Typically, tissue to be treated is identified and localized during treatment planning. Then, later during treatment sessions, the task is to reproduce the exact position as during the planning session.

A variety of techniques can be used for patient positioning Frequently some automatic registration procedure is deployed to recover the transformation that needs to be applied to the treatment couch to perform the alignment. However, it is typically the case that all planning data except the required position is ignored. This results in decreased accuracy of the automatic aligning. The root of the problems with the accuracy lies in the fact that all data points in a planning volume and a treatment volume are used equally when computing a mean square error (MSE).

SUMMARY OF THE INVENTION

The embodiments of the invention provide a weighting method, based on a planned radiation dose. The advantage of the method is that an optimization is forgiving of misalignment in the areas of the body where no radiation is delivered, but is more sensitive to misalignment in the affected areas and tissue-at-risk, than conventional uniform weighting methods.

The method implements a "soft" region-of-interest technique, that selectively weights the cost of misalignment proportional to a degree at which the given part of the tissue will be affected by the radiation. This allows for a more precise and accurate registration of the patient during radiation treatment.

DETAILED DESCRIPTION OF THE PREFERRED EMBODIMENTS

Figure 1:
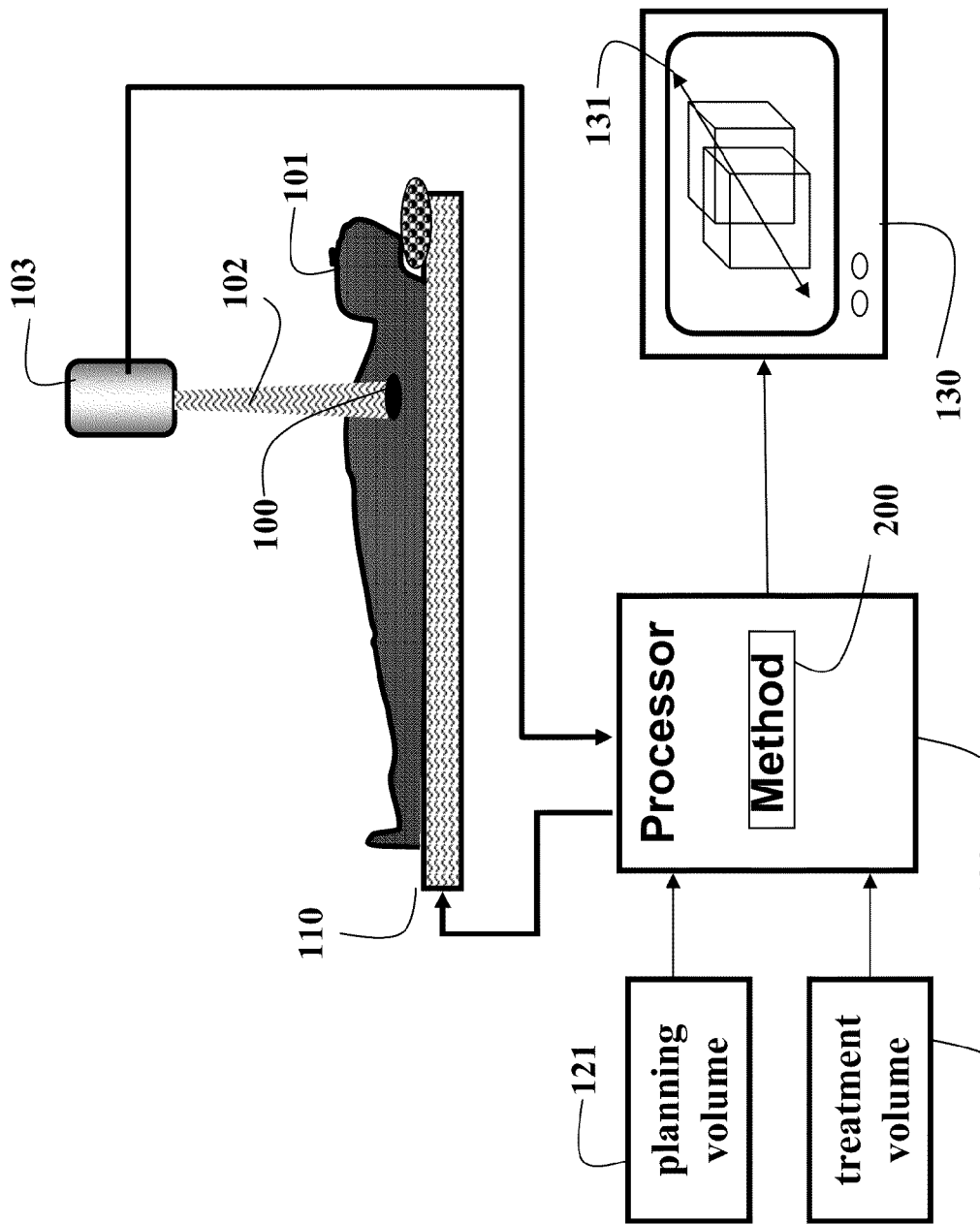
FIG. 1 is a block diagram of a system and method for plan-based medical image registration.

FIG. 1 shows a system 120 and method 200 for plan-based medical image registration for radiotherapy of a tumor 100 of a patient 101 by a radiation beam 102, e.g., a particle beam generated by a source 103 while the patient is positioned on a treatment couch 110.

During treatment planning a planning volume 121 is acquired. Then, later during radiotherapy, a treatment volume is acquired. The volumes can be acquired using some medical imaging technique, such as computed tomography (CT).

The idea is to align the treatment volume with the planning volume by applying a coordinate transformation 131 required to align the volumes also to the couch 110. The volumes can be visualized on a display device 130. Steps of the method 200, as described below, can be performed on the processor 120 including memory and input/output interfaces as known in the art.

The invention is based on the fact that not all areas in the treatment area of the patient are equally important in alignment. For instance, if there is no radiation that will be affecting a point in the tissue, it does not matter how accurately the tissue is aligned with the treatment plan. Conversely, it is critically important that the critical structures in the patient's body are positioned out of the radiation's reach. And finally, the treatment volume has to be positioned precisely as prescribed.

The method uses a constraint-based weighting scheme to deliver the more accurate alignment, which uses an output of a planning and dose calculation systems to arrive at a solution for the patient position which is potentially faster and more accurate than conventional methods, while also allowing for larger degrees of deformation in tissues.

Figure 2:
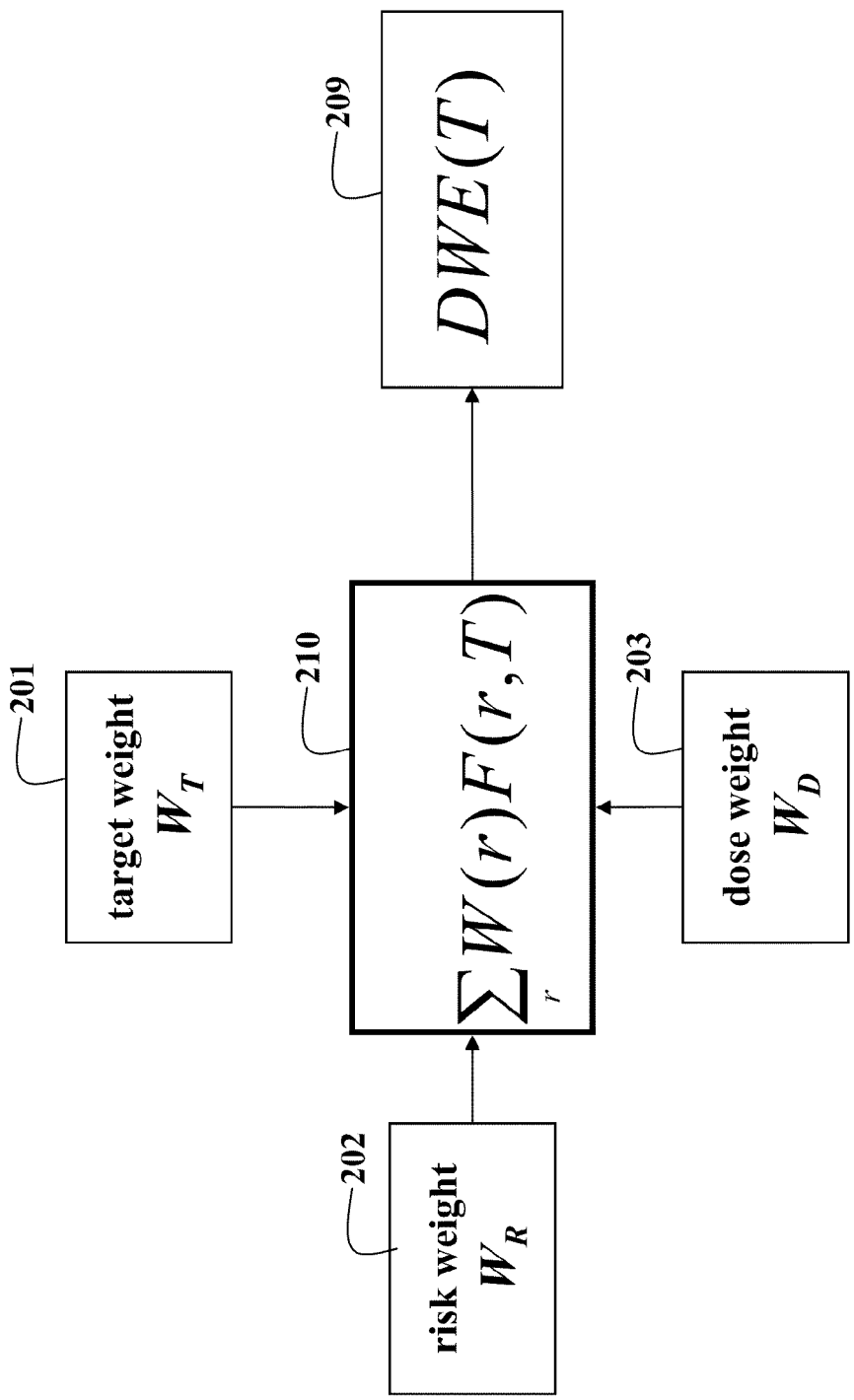
FIG. 2 is a flow diagram of the method for plan-based medical image registration according to embodiments of the invention.

As shown in FIG. 2, the method uses a formulation where contribution of each voxel r in the calculation of the error function is weighted in proportion to:

target weight $W_T$ 201,
tissue at risk exclusion weight $W_R$ 202, and
delivered dose weight $W_D$ 203.

The target weight is assigned to a voxel inside the prescribed target region to be treated. Because all weights are relative to each other, the weight can be any "reference weight," and other weights are expressed in terms of "more important" or "less important" than the target weight, e.g., $W_d < W_t \leq W_r$. The weights can be asymmetric for over and under-dosing in such a way that the weight $W_t$ penalizes underdose more than overdose, while the weight $W_r$ penalizes overdose more than underdose.

In many formulations, the overall misalignment error is calculated as a cumulative quantity, aggregated over all voxels in the medical images. For example, a simple mean squared error between the treatment volume and the planning volume for a transformation T, MSE(T), is calculated as:

$$MSE(T) = \sum_r (I(r) - V(T(r)))^2,$$

where T is a coordinate transformation, I is the treatment volume, V is the planning volume, and r are positions in the volumes to be aligned.

The method according to embodiments of the invention uses a weighted MSE determined as:

$$WE(T) = \sum_r [(W_T(r) + W_R(r) + W_D(r))(I(r) - V(T(r)))]^2.$$

More generally, a weighted error WE 209 is minimized 210 using an objective function F(r, T) weighted by a weighting function W(r):

$$WE(T) = \sum_r W(r) F(r, T),$$

where W(r) is some function of the weights $W_T(r)$, $W_R(r)$, $W_D(r)$, i.e., the target weight, tissue at risk weight and the delivered dose weight, respectively.

Although the invention has been described by way of examples of preferred embodiments, it is to be understood that various other adaptations and modifications can be made within the spirit and scope of the invention. Therefore, it is the object of the appended claims to cover all such variations and modifications as come within the true spirit and scope of the invention.

I claim:

1. A method for determining an error in aligning a patient with a radiation beam, comprising the steps of:
    acquiring a planning volume V during treatment planning;
    acquiring a treatment volume I during treatment; and
    minimizing, for each point r in the planning volume and treatment volume to be aligned by a coordinate transformation T, a weighted error DWE using an objective function F(r, T) applied to the planning volume and the treatment volume weighted by a weighting function W(r) as $$WE(T) = \sum_r W(r) F(r, T),$$

where W(r) is a function of a target weight $W_T$, a tissue at risk weight $W_R$, and a delivered dose weight $W_D$, wherein the minimizing is performed in a processor.

2. The method of claim 1, wherein $$WE(T) = \sum_r [(W_T(r) + W_R(r) + W_D(r))(I(r) - V(T(r)))]^2.$$

3. The method of claim 2, wherein the weight are $W_d < W_t \leq W_r$.

4. The method of 1, wherein the radiation beam is a particle beam.

* * * * *